(12) United States Patent
Rotman et al.

(10) Patent No.: US 10,556,102 B1
(45) Date of Patent: Feb. 11, 2020

(54) AUTOMATIC ADJUSTMENT OF ELECTRODE SURFACE IMPEDANCES IN MULTI-ELECTRODE CATHETERS

(71) Applicant: Biosense Webster (Israel) Ltd., Yokneam (IL)

(72) Inventors: Eyal Rotman, Kiriat Tivon (IL); Michael Levin, Haifa (IL); Yevgeny Bonyak, Haifa (IL); Alek Vilensky, Netanya (IL); Meir Bar-Tal, Haifa (IL); Oleg Dulger, Zichron Taakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 59 days.

(21) Appl. No.: 16/102,187

(22) Filed: Aug. 13, 2018

(51) Int. Cl.
*A61N 1/05* (2006.01)
*A61B 5/00* (2006.01)
*A61B 5/04* (2006.01)
*A61B 5/042* (2006.01)
*A61N 1/04* (2006.01)
*A61B 5/0408* (2006.01)

(52) U.S. Cl.
CPC .............. *A61N 1/05* (2013.01); *A61B 5/04* (2013.01); *A61B 5/6852* (2013.01); *A61B 5/042* (2013.01); *A61B 5/0408* (2013.01); *A61B 5/6846* (2013.01); *A61N 1/04* (2013.01); *A61N 1/0476* (2013.01)

(58) Field of Classification Search
CPC ... A61N 1/00; A61N 1/02; A61N 1/04; A61N 1/0476; A61N 1/05; A61B 5/00; A61B 5/04; A61B 5/0408; A61B 5/04085; A61B 5/042; A61B 5/0422; A61B 5/0424; A61B 5/68; A61B 5/6846; A61B 5/6847; A61B 5/6852

USPC ....... 324/600, 612, 613, 620, 649, 691, 713, 324/715, 718, 722, 724, 500, 512, 525, 324/527, 537; 600/372, 373, 374, 393; 606/1, 32, 34, 41, 45, 48, 49, 50, 129; 607/1, 115, 116, 119, 122
See application file for complete search history.

(56) References Cited

U.S. PATENT DOCUMENTS

| | | | |
|---|---|---|---|
| 4,322,805 A | * | 3/1982 | Rog ............... G01N 17/02 324/323 |
| 4,721,551 A | | 1/1988 | Byers et al. |
| 5,980,705 A | | 11/1999 | Allen et al. |

(Continued)

OTHER PUBLICATIONS

Buchthal, Fritz et al., "Volume Conduction of the Spike of the Motor Unit Potential Investigated with a New Type of Multielectrode", Acta Physiol. Scand., (1957), pp. 331-354, vol. 38.

(Continued)

*Primary Examiner* — Hoai-An D. Nguyen
(74) *Attorney, Agent, or Firm* — Vincent J. Serrao

(57) ABSTRACT

An apparatus includes a controllable signal source and a processor. The controllable signal source is configured to apply an Alternating Current (AC) signal to multiple electrodes of a multi-electrode catheter immersed in an aquatic solution. The processor is configured to, responsively to the applied AC signal, estimate a respective surface impedance or a respective electrical noise level of each of the electrodes. The processor is further configured to disconnect each electrode, independently of other electrodes, when the estimated surface impedance or electrical noise level of the electrode drops below a preset value.

10 Claims, 3 Drawing Sheets

(56) References Cited

U.S. PATENT DOCUMENTS

| | | | | |
|---|---|---|---|---|
| 6,377,052 | B1* | 4/2002 | McGinnis | G01N 27/02 |
| | | | | 324/439 |
| 9,717,552 | B2* | 8/2017 | Cosman | A61B 18/1482 |
| 9,743,975 | B2* | 8/2017 | Brannan | A61B 18/14 |
| 2002/0123749 | A1* | 9/2002 | Jain | A61B 18/1492 |
| | | | | 606/41 |
| 2006/0259109 | A1 | 11/2006 | Zhou et al. | |
| 2009/0177071 | A1 | 7/2009 | Harlev et al. | |
| 2010/0168735 | A1* | 7/2010 | Deno | A61B 5/053 |
| | | | | 606/34 |
| 2010/0274150 | A1 | 10/2010 | Harlev et al. | |
| 2015/0320480 | A1* | 11/2015 | Cosman, Jr. | A61B 90/37 |
| | | | | 606/34 |
| 2016/0018347 | A1* | 1/2016 | Drbal | A61M 1/288 |
| | | | | 210/647 |
| 2016/0200573 | A1* | 7/2016 | Yokota | C02F 1/4672 |
| | | | | 423/580.1 |
| 2017/0219399 | A1* | 8/2017 | Kung | G01F 1/584 |
| 2018/0345006 | A1* | 12/2018 | Ambrose | A61N 1/36025 |

OTHER PUBLICATIONS

De Luca, Carlo J. et al., "An Electrode for Recording Single Motor Unit Activity during Strong Muscle Contractions", IEEE Transactions on Biomedical Engineering, Sep. 1972, pp. 367-372, vol. BME-19, No. 5.

Gielen, F.L.H et al., "Comparison of electrode impedances of Pt, PtIr (10% Ir) and Ir-AIROF electrodes used in electrophysiological experiments", Medical & Biological Engineering & Computing, Jan. 1982, pp. 77-83, vol. 20.

\* cited by examiner

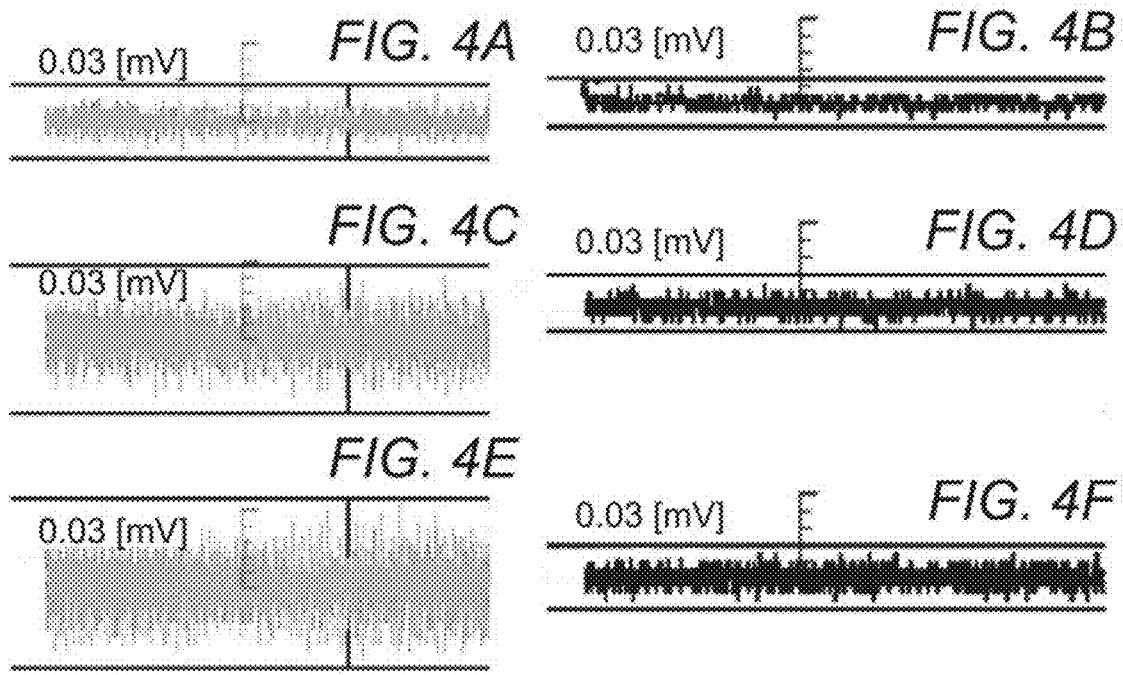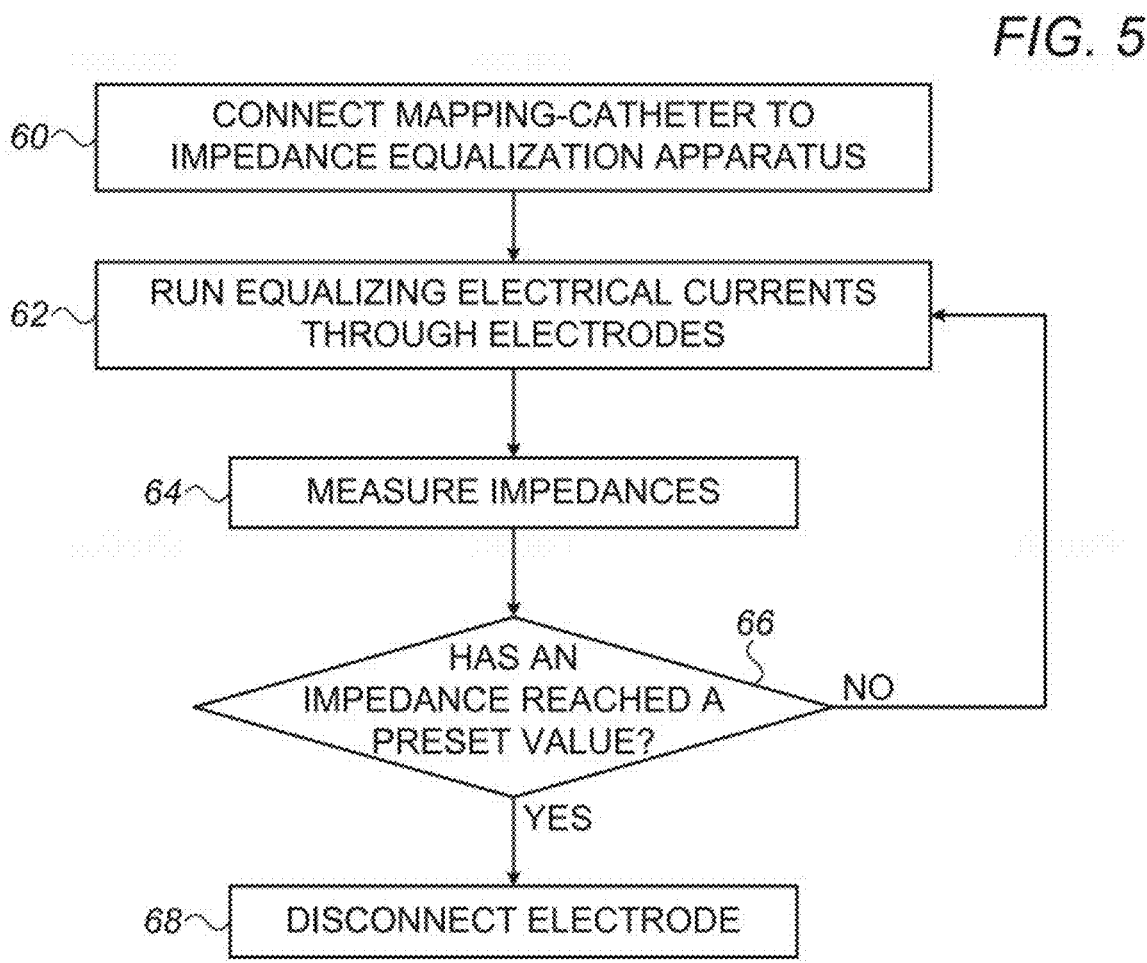

AUTOMATIC ADJUSTMENT OF ELECTRODE SURFACE IMPEDANCES IN MULTI-ELECTRODE CATHETERS

FIELD OF THE INVENTION

The present invention relates generally to medical probes, and particularly to electro-physiological sensing catheters.

BACKGROUND OF THE INVENTION

Various known techniques were proposed for improving the electrical properties of biocompatible electrodes. For example, in "An Electrode for Recording Single Motor Unit Activity during Strong Muscle Contractions," IEEE Transactions on Biomedical Engineering, Vol. BME-19, No. 5, September, 1972, pages 367-372, De Luca and Forrest describe the construction of a lightweight needle electrode offering four monopolar and six bipolar microelectrode combinations. An electrolytic treatment for reducing the impedance of the electrode is described. The frequency response of twelve monopolar and twelve bipolar microelectrodes was measured before the electrolytic treatment, ten minutes after the electrolytic treatment, and 72 hours after the electrolytic treatment. The Bode form was used to synthesize a simple resistance-capacitance (RC) model for each of the three situations, giving some insight to the physical change at the tip of the electrode. As another example, in "Comparison of Electrode Impedances of Pt, PtIr (10% Ir) and Ir-AIROF Electrodes Used in Electro-physiological Experiments," Medical & Biological Engineering & Computing, January, 1982, volume 20, pages 77-83, Gielen and Bergveld describe tissue impedance measurements with four-electrode assembly, encountered by unexpected difficulties because of a combination of electrode impedance and stray capacitance in the array of four electrodes, which could lead to serious measuring failures in the low-frequency range. The publication describes using electrolytic etching to enlarge the effective surface of electrodes, resulting in lower electrode impedances. The etching was achieved by applying a sinusoidal voltage between the electrode and a large indifferent Pt-ring electrode both immersed in a saline solution.

U.S. Pat. No. 4,721,551 describes a method for electroplating iridium metal onto the surface of a metallic microelectrode for use in a biomedical prosthetic device. Another aspect of the method discloses conditioning the microelectrode by storage for between about 6 and 150 hours in a physiologically equivalent phosphate buffered saline solution selected under in vitro conditions. Further conditioning of the microelectrode is done by applying between about positive 1 and negative 1 volts for between 100 and 10,000 millivolts per second, for between about 1 and 100 cycles to form at least one iridium oxide on the surface of the microelectrode.

SUMMARY OF THE INVENTION

An embodiment of the present invention provides an apparatus including a controllable signal source and a processor. The controllable signal source is configured to apply an Alternating Current (AC) signal to multiple electrodes of a multi-electrode catheter immersed in an aquatic solution. The processor is configured to, responsively to the applied AC signal, estimate a respective surface impedance or a respective electrical noise level of each of the electrodes. The processor is further configured to disconnect each electrode, independently of other electrodes, when the estimated surface impedance or electrical noise level of the electrode drops below a preset value.

In some embodiments, the apparatus further includes a user interface configured to receive from a user, output parameters of the controllable signal source, and the processor is configured to configure the controllable signal source with the output parameters received from the user.

In some embodiments, the apparatus further includes a respective resistor connected in series with each electrode, and the processor is configured to sense a respective voltage drop across each resistor, and to estimate the surface impedance or electrical noise level of the electrode responsively to the voltage drop.

In an embodiment, the apparatus further includes a respective switch connected in series with each electrode, and the processor is configured to disconnect each electrode by controlling the respective switch.

In another embodiment, the processor is configured to set the preset value based on a result of a previous adjustment process of the surface impedance or electrical noise level.

There is additionally provided, in accordance with an embodiment of the present invention, a method, including applying an Alternating Current (AC) signal to multiple electrodes of a multi-electrode catheter immersed in an aquatic solution. A respective surface impedance or a respective electrical noise level of each of the electrodes is estimated responsively to the applied AC signal. Each electrode is disconnected, independently of other electrodes, when the estimated surface impedance or electrical noise level of the electrode drops below a preset value.

The present invention will be more fully understood from the following detailed description of the embodiments thereof, taken together with the drawings in which:

BRIEF DESCRIPTION OF THE DRAWINGS

FIGS. 4A-4F are graph pairs showing measured electrical noises generated by micro-electrodes before and after a conditioning process, in accordance with an embodiment of the present invention; and FIG. 5 is a flow chart that schematically illustrates a method for equalizing impedances of micro-electrodes, in accordance with an embodiment of the present invention.

DETAILED DESCRIPTION OF EMBODIMENTS

Overview

Figure 1:
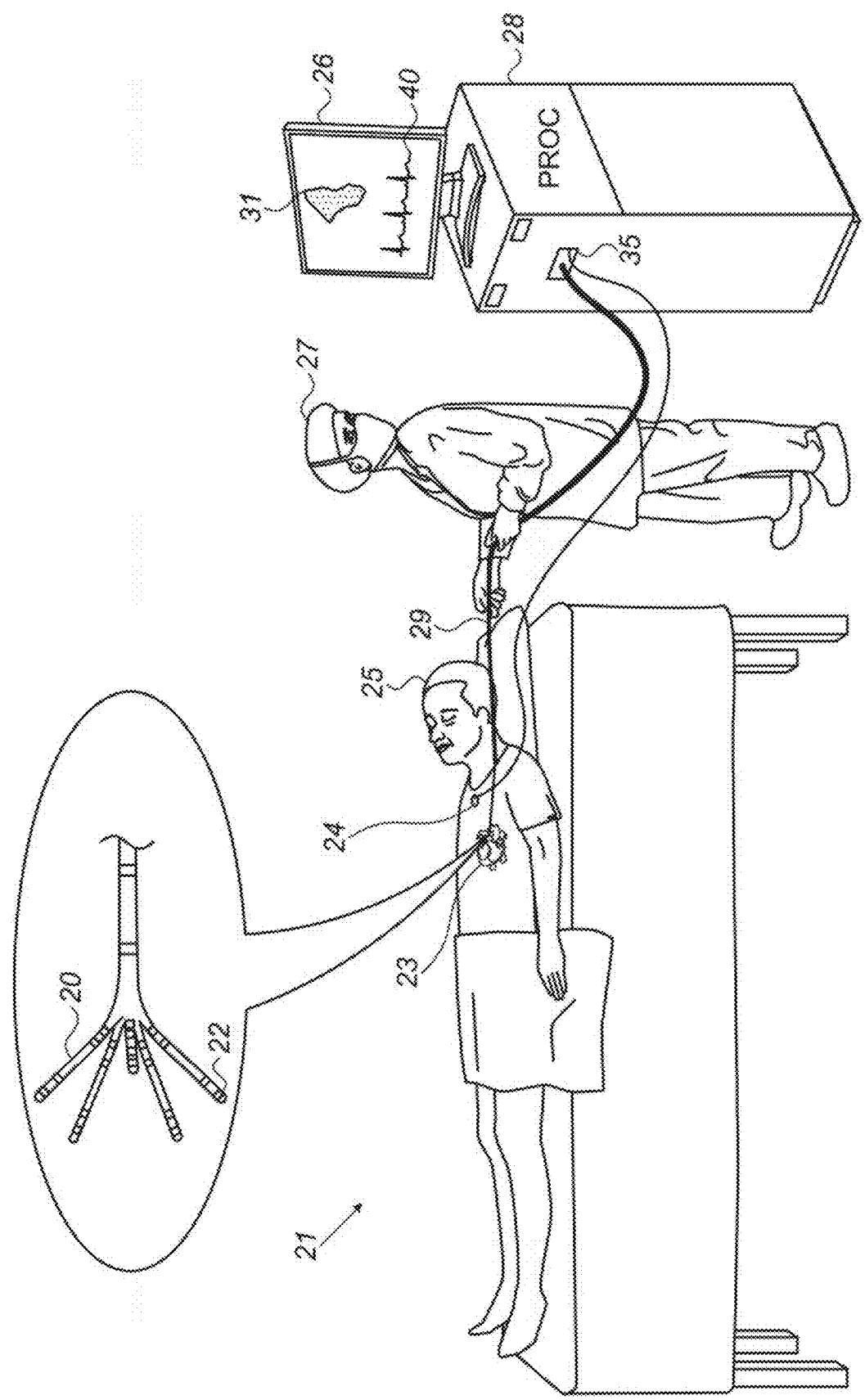
FIG. 1 is a schematic, pictorial illustration of a catheter-based electro-physiological mapping system, in accordance with an embodiment of the present invention.

A mapping-catheter may be introduced into the heart of a patient to diagnose an electro-physiological condition such as an arrhythmia. Using electrodes fitted at the distal-end of a catheter, a physician may then acquire electro-physiological signals that are indicative of the nature and locations of one or more intra-cardiac sites responsible for the electrophysiological medical condition. The physician may then perform a local treatment, such as an intra-cardiac ablation.

Local measurements of electrical potentials of tissue may be performed utilizing two adjacent small-area electrodes, i.e., in a bipolar signal acquisition geometry. For performing such bipolar measurements in an organ such as a heart, the electrodes are fitted at the distal end of a probe, such as at a distal end of an electrophysiological mapping-catheter, which is inserted into the heart. Additionally or alternatively, the same catheter may be used in a unipolar measurement geometry, in which one or more of the small-area electrodes measure cardiac tissue electro-potentials relative to one or more surface electrodes attached to the skin.

Various problems with the surface quality of the small-area electrodes may cause the electro-physiological signal to suffer from undesired artifacts, whether using bipolar or unipolar sensing geometry. Such disturbances may include low-frequency noises (e.g., baseline wander) and/or high-frequency white noise. Such noises may hinder a robust clinical diagnosis based on the measurements performed during the invasive procedure.

Embodiments of the present invention that are described hereinafter equalize the surface impedances of the small-area electrodes (also termed hereinafter "micro-electrodes") of a multi-electrode catheter, and/or the electrical noises generated by the small-area electrodes, resulting in superior signal quality. The improvement in measured signal quality may be evident, for example, in intra-cardiac electrocardiogram (ECG) signals acquired by micro-electrodes fitted at a distal end of a catheter using bipolar measurement geometry.

In some embodiments, a method of micro-electrode conditioning by electrolysis is provided, which includes automatically equalizing, within a given tolerance, surface impedances of all micro-electrodes to a preset minimal value. The method is based on passing electrical current of low amplitude (e.g., from several μA to several mA) and low frequency (e.g., several Hertz to tens of Hertz) between each of the electrodes and a return electrode (i.e., common ground), while the electrodes and the return electrode are placed in an aquatic solution (e.g., a saline solution).

In an embodiment, a signal source generates the electrical current described above. A controllable signal source applies the electrical current to the electrodes. During the electrolysis process, a processor continuously estimates the impedances between each of the micro-electrodes and the return electrode, e.g., using voltage measurements in real-time. To equalize the impedances, whenever an individual micro-electrode impedance reaches a preset minimal value, the processor automatically (and independently of the rest of the electrodes) disconnects the micro-electrode from the signal source so that the process of electrode conditioning by electrolysis stops. The entire process of conditioning the set of micro-electrodes ends when all of the micro-electrodes reach the required preset minimal impedance value and are all disconnected from the signal source.

In an alternative embodiment, a variant of the disclosed method is applied for conditioning the electrodes based on measuring, in real-time, electrical noises generated by the micro-electrodes and, independently disconnecting each micro-electrode from electrolysis when the electrode noise drops below a preset noise value.

The disclosed techniques for improving the quality of electro-physiological signals acquired using micro-electrodes may assist in providing a robust clinical diagnosis outcome of an invasive procedure. In this way, the disclosed techniques may improve the overall efficacy of an invasive procedure, such as cardiac catheterization.

System Description

FIG. 1 is a schematic, pictorial illustration of a catheter-based electro-physiological mapping system 21, in accordance with an embodiment of the present invention. FIG. 1 depicts a physician 27 using an electro-anatomical mapping catheter 29 to perform an electro-anatomical mapping of a heart 23 of a patient 25. Mapping catheter 29 comprises, at its distal end, one or more arms 20, each of which is coupled to one or more electrodes 22.

During the mapping procedure, while electrodes 22 are inside heart 23 of the patient, the locations of electrodes 22 are tracked. For that purpose, electrical signals are passed between electrodes 22 and external electrodes 24. For example, three external electrodes 24 may be coupled to the patient's chest, and another three external electrodes may be coupled to the patient's back. (For ease of illustration, only one external electrode is shown in FIG. 1.)

Based on the signals, and given the known positions of electrodes 24 on the patient's body, processor 28 calculates an estimated location of each of electrodes 22 within the patient's heart. Respective electrophysiological data, such as intracardiac ECG traces, are additionally acquired from tissue of heart 23 by using electrodes 22. The processor may thus associate any given signal received from electrodes 22, such as an electrophysiological signal, with the location at which the signal was acquired. A processor 28 receives the resulting signals via an electrical interface 35, and uses information contained in these signals to construct an electrophysiological map 31 and ECG traces 40, and to present these on a display 26.

The example illustration shown in FIG. 1 is chosen purely for the sake of conceptual clarity. Other types of electro-physiological sensing catheter geometries, such as the Lasso® Catheter (produced by Biosense-Webster Inc., Irvine, Calif.) may be employed. Additionally, contact sensors may be fitted at the distal end of mapping catheter 29 and transmit data indicative of the physical quality of electrode contact with tissue. In an embodiment, measurements of one or more electrodes 22 may be discarded if their physical contact quality is indicated as poor, and the measurements of other electrodes may be regarded as valid if their contact quality is indicated as sufficient.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Automatic Adjustment of Electrode Impedances

Figure 2:
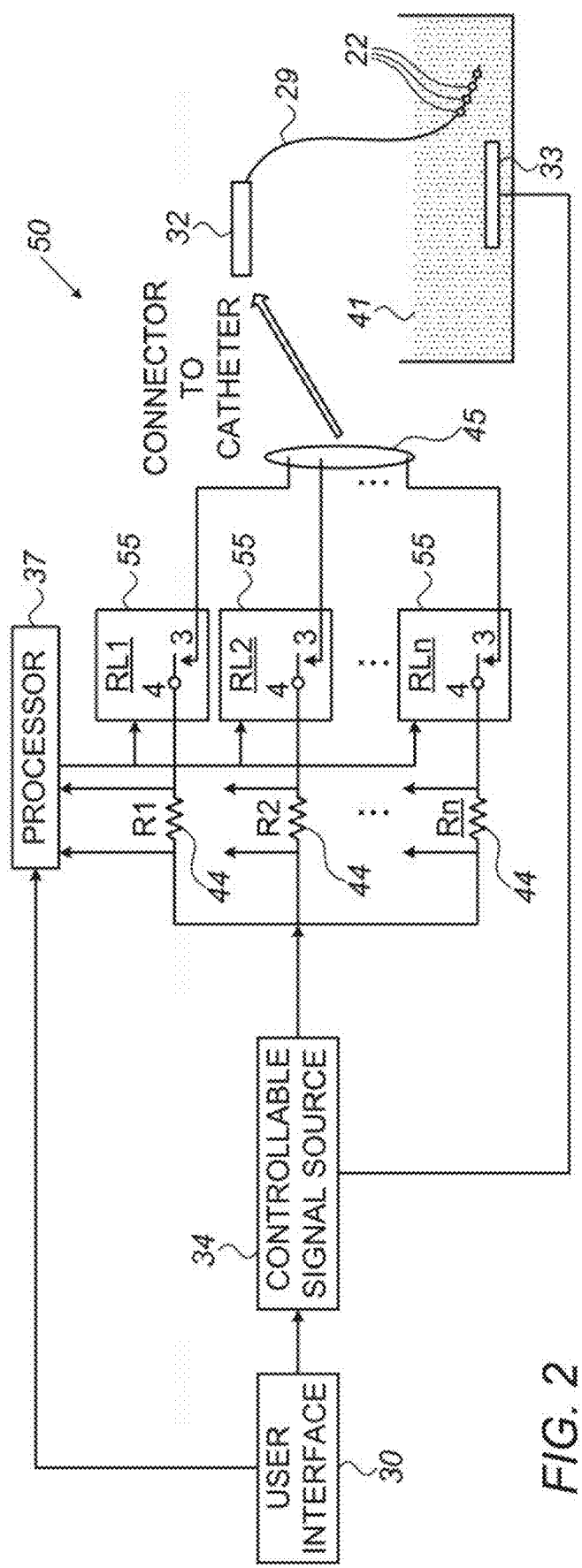
FIG. 2 is a schematic block diagram of an electrochemical apparatus for equalizing surface impedances of micro-electrodes of a multi-electrode catheter, in accordance with an embodiment of the present invention.

FIG. 2 is a schematic block diagram of an electrochemical apparatus 50 for equalizing surface impedances of micro-electrodes 22 of multi-electrode catheter 29, in accordance with an embodiment of the present invention. As seen, micro-electrodes 22 are immersed in a bath 41 filled with saline solution, which causes electrolysis conditions when current flows between electrodes 22 and a return electrode 33, which is also immersed in bath 41. Catheter 29 is electrically connected to apparatus 50 via a connector 45 at a handle 32 of the catheter.

A user interface 30 of apparatus 50 is connected to a controllable alternating current (AC) signal source 34 and to a processor 37. User interface 30 allows a user to set the output parameters of controllable signal source 34 and to preset target electrical impedance and/or electrical noise values, at which limit processor 37 stops electrolysis.

During electrolysis, signal source 34 drives a number N, N≥2, of independent AC currents through respective micro-electrodes 22. Electrode 33 forms the return path for the AC currents. A respective switch, e.g., a relay 55, is configured to selectably disconnect each electrode 22 from signal source 34 through opening a contact '3-4' of the relay. Relays 55 are controlled by processor 37.

During electrolysis, processor 37 evaluates the individual electrical currents flowing through electrodes 22 by measuring the respective voltage drops on serial resistors 44 $R_1$ to $R_N$. Processor 37 is configured to independently switch off (i.e., disconnect) each of relays 55 so as to disconnect a respective electrode 22 when an evaluated impedance of the electrode connected via the channel reaches a preset target minimal impedance value and/or when an evaluated electrical noise drops under a preset electrical noise value.

The example illustration shown in FIG. 2 is chosen purely for the sake of conceptual clarity. FIG. 2 shows only parts relevant to embodiments of the present invention. For example, processor 37 may measure RMS values, or peak-to-peak values, of a noise of the voltage drop on the serial resistors 44 $R_1$ to $R_N$. Alternatively to using a voltage source, controllable signal source 34 may comprise a current source with processor 37 measuring the varying voltages that drop on serial resistors 44 $R_1$ to $R_n$ during the conditioning process. Other system elements, such as a digital oscilloscope, may be used and are omitted for simplicity of presentation.

Figure 3B:
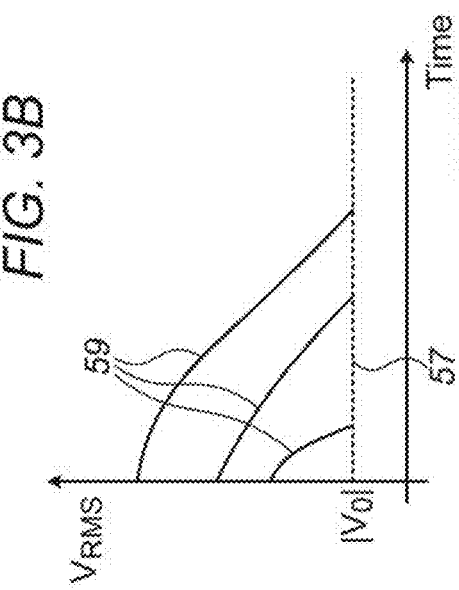
FIGS. 3A and 3B are schematic graphs that illustrate a conditioning process to equalize either impedances, or electrical noises, of micro-electrodes, in accordance with an embodiment of the present invention.
Figure 3A:
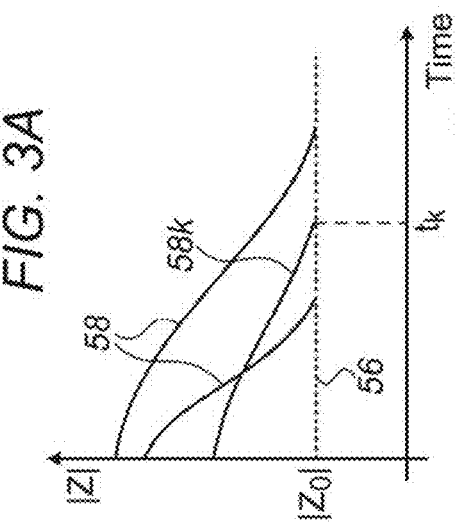

FIGS. 3A and 3B are schematic graphs that illustrate a conditioning process to equalize either impedances, or electrical noises of micro-electrodes, in accordance with an embodiment of the present invention. FIG. 3A shows impedance-magnitude curves 58 of electrodes 22 measured as a function of duration of conditioning. As seen, at the beginning of the conditioning process (time=0), initial values of impedance-magnitudes 58 vary between electrodes. As the currents flow through the different electrodes, their impedance-magnitudes drop, each in an individual manner. As an impedance-magnitude of a given electrode, such as an electrode 22k having impedance-magnitude curve 58k, reaches a preset impedance-magnitude 56 $|Z_o|$ at a time $t_k$, processor 37 switches off the channel k relay. The impedance equalizing (i.e., conditioning) process for electrode 22k is then terminated. As seen in FIG. 3A, various electrodes have different durations of treatment for their impedance-magnitudes to reach value preset $|Z_o|$.

Alternatively, in some embodiments, apparatus 50 is used for equalizing, up to a given tolerance, peak-to-peak electrical noise generated by electrodes 22, which is presented, for example, in voltage RMS. A similar conditioning process is applied by apparatus 50, shown in FIG. 3B, where processor 37, instead of measuring impedances, analyzes electrical noises in measured voltages, which drop individually with time as curves 59 show. A preset target value for maximum RMS electrical noise is given by electrical noise limit 57 in voltage units, $|V_o|$. As an individual channel's analyzed noise reaches a value under $|V_o|$, processor 37 responsively terminates the conditioning of the electrode by switching off a respective relay 55.

The pictorial illustrations shown in FIGS. 3A and 3B are chosen purely for the sake of conceptual clarity. The actual form of curves 58 and curves 59 may vary. Preset impedance 56 and RMS electrical noise 57 may be have values that are larger or smaller relative to end points than those illustrated for curves 58 and curves 59, respectively.

FIGS. 4A-4F are graph pairs showing measured electrical noises generated by micro-electrodes before and after a conditioning process, in accordance with an embodiment of the present invention. Graphs of FIGS. 4A, 4C, and 4E show traces of measured noise (presented as fluctuations of a voltage) before undergoing noise minimization by electrochemical apparatus 50. As seen, the peak-to-peak noise in FIG. 4E, generated by an unconditioned electrode, is more than double the noise generated by another unconditioned electrode, shown in FIG. 4A. After the disclosed electrical noise equalization process, the peak-to-peak noise values of the electrodes become smaller and very similar, within a given tolerance, as shown by respective graphs brought by FIGS. 4B, 4D, and 4F.

FIG. 5 is a flow chart that schematically illustrates a method for equalizing impedances of micro-electrodes 22, in accordance with an embodiment of the present invention. The process begins with electrically connecting catheter 29 to apparatus 50, and immersing electrodes 22 in a saline bath 41, at a preparatory step 60.

Next, the process of equalizing impedances begins, by signal source 34 applying electrolyzing currents, at a conditioning process step 62. The individual impedances of electrodes 22 are periodically measured during the conditioning process by processor 37, at a measurement step 64. Processor 37 compares the evaluated impedances to a preset impedance value, at a comparison step 66. If an impedance of a given electrode 22 reaches the preset value, then processor 37 disconnects the electrode to stop electrolysis. If an impedance has not yet reached the preset value, the conditioning process continues by looping to conditioning process step 62.

In some embodiments, both the preset impedance value and the given tolerance are set before starting each individual conditioning process of a set of electrodes. For example, the target impedance value is preset as the lowest measured impedance among electrodes 22 of the catheter. In another embodiment, processor 37 sets the preset impedance based on statistical analysis of impedance values achieved in previous equalizing processes (i.e., based on analyzing electrode impedance data of electrodes that underwent the disclosed process for equalizing surface impedances). Similarly, processor 37 may set the preset noise level based on statistical analysis of noise levels achieved in previous equalizing processes.

The example flow chart shown in FIG. 5 is chosen purely for the sake of conceptual clarity. In an alternative embodiment, processor 37 analyzes and compares electrical noises generated by each electrode to a preset noise value. Processor 37 terminates the conditioning process 62 of an electrode when the electrical noise generated by the electrodes drops below the preset noise value, as indicated by processor 37.

Although the embodiments described herein mainly address invasive cardiac applications, the methods and systems described herein can also be used in other applications, such as invasive neurology procedures. The methods and systems described herein can also be used with electrodes intended for non-invasive procedures, such as the recording of an electroencephalogram (EEG).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
    a controllable signal source configured to apply an Alternating Current (AC) signal to multiple electrodes of a multi-electrode catheter immersed in an aquatic solution; and
    a processor, configured to:
        responsively to the applied AC signal, estimate a respective surface impedance or a respective electrical noise level of each of the electrodes; and
        disconnect each electrode, independently of other electrodes, when the estimated surface impedance or electrical noise level of the electrode drops below a preset value.

2. The apparatus according to claim 1, and comprising a user interface configured to receive from a user output parameters of the controllable signal source, wherein the processor is configured to configure the controllable signal source with the output parameters received from the user.

3. The apparatus according to claim 1, and comprising a respective resistor connected in series with each electrode, wherein the processor is configured to sense a respective voltage drop across each resistor, and to estimate the surface impedance or electrical noise level of the electrode responsively to the voltage drop.

4. The apparatus according to claim 1, and comprising a respective switch connected in series with each electrode, wherein the processor is configured to disconnect each electrode by controlling the respective switch.

5. The apparatus according to claim 1, wherein the processor is configured to set the preset value based on a result of a previous adjustment process of the surface impedance or electrical noise level.

6. A method, comprising:
    applying an Alternating Current (AC) signal to multiple electrodes of a multi-electrode catheter immersed in an aquatic solution;
    responsively to the applied AC signal, estimating a respective surface impedance or a respective electrical noise level of each of the electrodes; and
    disconnecting each electrode, independently of other electrodes, when the estimated surface impedance or electrical noise level of the electrode drops below a preset value.

7. The method according to claim 6, and comprising receiving from a user parameters of the AC signal, and configuring the AC signal with the parameters received from the user.

8. The method according to claim 6, wherein estimating the surface impedance or electrical noise level of each electrode comprises sensing a respective voltage drop across a respective resistor connected in series with each electrode, and estimating the surface impedance or electrical noise level of the electrode responsively to the voltage drop.

9. The method according to claim 6, wherein disconnecting each electrode comprises controlling a respective switch connected in series with each electrode.

10. The method according to claim 6, and comprising setting the preset value based on a result of a previous adjustment process of the surface impedance or electrical noise level.

* * * * *